(12) United States Patent
Devries et al.

(10) Patent No.: US 12,226,147 B2
(45) Date of Patent: *Feb. 18, 2025

(54) MEDICAL DEVICE CAPABLE OF INJECTION, CUTTING AND COAGULATION

(71) Applicant: BOSTON SCIENTIFIC SCIMED, INC., Maple Grove, MN (US)

(72) Inventors: Robert B. Devries, Northborough, MA (US); Peter L Dayton, Brookline, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 230 days.

This patent is subject to a terminal disclaimer.

(21) Appl. No.: 18/062,990

(22) Filed: Dec. 7, 2022

(65) Prior Publication Data

US 2023/0116333 A1    Apr. 13, 2023

Related U.S. Application Data

(63) Continuation of application No. 16/400,575, filed on May 1, 2019, now Pat. No. 11,534,233, which is a continuation of application No. 15/409,255, filed on Jan. 18, 2017, now Pat. No. 10,321,952.

(60) Provisional application No. 62/287,207, filed on Jan. 26, 2016.

(51) Int. Cl.
*A61B 18/12* (2006.01)
*A61B 18/14* (2006.01)
*A61B 18/00* (2006.01)

(52) U.S. Cl.
CPC ...... *A61B 18/1477* (2013.01); *A61B 18/1206* (2013.01); *A61B 2018/00601* (2013.01); *A61B 2018/1253* (2013.01); *A61B 2018/126* (2013.01); *A61B 2018/1425* (2013.01); *A61B 2018/1427* (2013.01);
(Continued)

(58) Field of Classification Search
CPC .................................................. A61B 18/1206
See application file for complete search history.

(56) References Cited

U.S. PATENT DOCUMENTS

| | | | | |
|---|---|---|---|---|
| 4,532,924 A | * | 8/1985 | Auth | A61B 18/14 606/50 |
| 5,342,381 A | * | 8/1994 | Tidemand | A61B 18/1445 606/174 |

(Continued)

*Primary Examiner* — Daniel W Fowler
(74) *Attorney, Agent, or Firm* — Fay Kaplun & Marcin, LLP

(57) ABSTRACT

A device for treating tissue includes a catheter including an elongated body extending from a proximal end to a distal end and including a lumen extending therethrough, a distal tip connected to the distal end of the elongated body and including a first electrode and a second electrode extending thereabout, the first electrode extending to a distal opening of the lumen and a first needle extending longitudinally from a proximal end to a distal end, the first needle slidably received within the lumen of the catheter to be moved between a retracted bipolar configuration, in which the distal end of the needle is proximal the distal opening of the catheter, and an extended monopolar configuration, in which the distal end of the first needle extends distally past the distal opening of the catheter so that the first needle contacts the first electrode and is configured to cut tissue.

17 Claims, 7 Drawing Sheets

(52) U.S. Cl.
CPC .......... *A61B 2018/1435* (2013.01); *A61B 2018/1475* (2013.01); *A61B 2217/007* (2013.01)

(56) References Cited

U.S. PATENT DOCUMENTS

| | | | | |
|---|---|---|---|---|
| 5,383,876 | A * | 1/1995 | Nardella | A61B 18/1477 606/49 |
| 5,403,311 | A * | 4/1995 | Abele | A61B 18/1492 606/49 |
| 5,683,388 | A * | 11/1997 | Slater | A61B 10/06 606/41 |
| 7,537,595 | B2 * | 5/2009 | McClurken | A61B 18/1492 606/50 |
| 2005/0043728 | A1 * | 2/2005 | Ciarrocca | A61B 18/1482 606/50 |
| 2006/0189972 | A1 * | 8/2006 | Grossman | A61B 18/1477 606/41 |
| 2013/0178845 | A1 * | 7/2013 | Smith | A61B 18/1492 606/41 |
| 2015/0094719 | A1 * | 4/2015 | Batchelor | A61B 18/1485 606/50 |

* cited by examiner

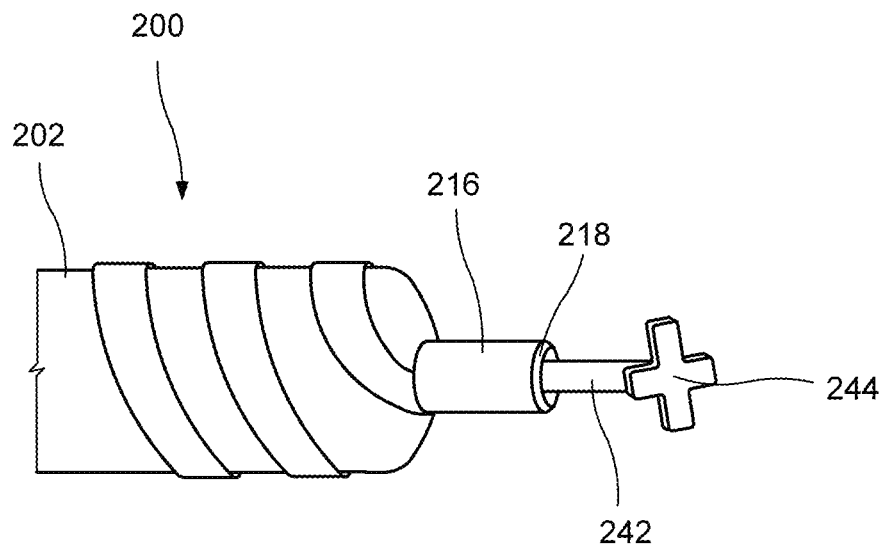
F I G. 9D
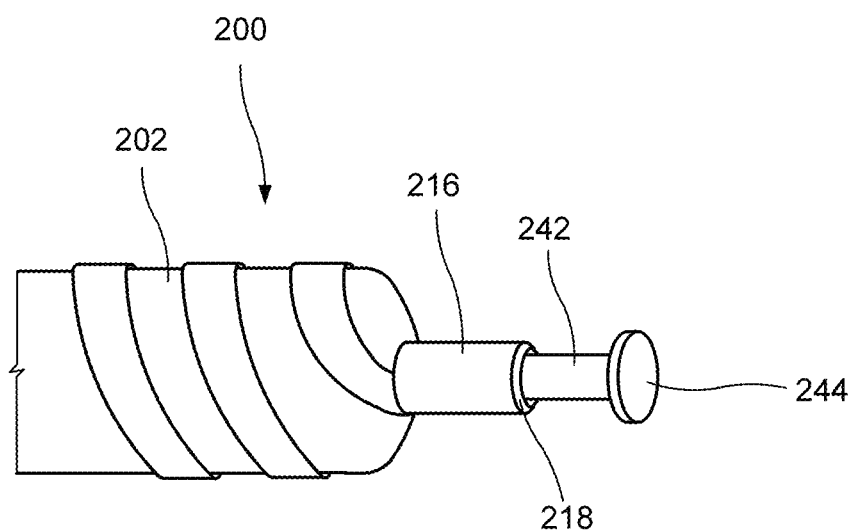
F I G. 9E

MEDICAL DEVICE CAPABLE OF INJECTION, CUTTING AND COAGULATION

PRIORITY CLAIM

This present application is a Continuation of U.S. patent application Ser. No. 16/400,575 filed May 1, 2019; which is a Continuation of U.S. patent application Ser. No. 15/409,255 filed Jan. 18, 2017, now U.S. Pat. No. 10,321,952; which claims priority to U.S. Provisional Patent Application Ser. No. 62/287,207 filed Jan. 26, 2016. The disclosures of the above application(s)/patent(s) are incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating or damaging the wall of the GI tract, or may require closure of the GI tract wall as part of the procedure. One method for sealing potential hemorrhaging or bleeding areas is via electrical coagulation of the target site. An electro-coagulation device may be inserted through the endoscope to the target site. In some cases, however, additional treatment of the tissue (e.g., ablation, cutting) may be necessary to treat the target site so that physicians may be required to use different devices to treat the target site as desired. The exchange of different devices through the endoscope may be time consuming, may increase the risk to the patient and may also increase patient discomfort.

SUMMARY

The present disclosure is directed to a device for treating tissue, comprising a catheter including an elongated body and a distal tip, the elongated body extending from a proximal end to a distal end and including a lumen extending therethrough, the distal tip connected to the distal end of the elongated body and including a first electrode and a second electrode extending thereabout, the first electrode extending to a distal opening of the lumen, and a first needle extending longitudinally from a proximal end to a distal end, the first needle slidably received within the lumen of the catheter to be moved between a retracted bipolar configuration, in which the distal end of the needle is proximal the distal opening of the catheter, and an extended monopolar configuration, in which the distal end of the first needle extends distally past the distal opening of the catheter so that the first needle contacts the first electrode and is configured to cut tissue.

In one embodiment, the first electrode may be connected to a power source supplying a current thereto.

In one embodiment, the second electrode may be electrically connected to a proximal portion of the first needle to provide a return path for the current.

In one embodiment, the second electrode may be connected to the proximal portion of the first needle via a conductive pad biased against the first needle.

In one embodiment, the first needle may be formed of a conductive material and may include an insulated portion which, when the first needle is in the extended monopolar configuration extends over the conductive pad to break the return path and inactivate the second electrode.

In one embodiment, the first needle may include a channel extending longitudinally therethrough and the proximal end of the needle may be configured to be coupled to one of a fluid source and a vacuum source.

In one embodiment, the first needle may be formed of a non-conductive material and may include a metal strip extending along a length thereof.

In one embodiment, the first needle may include a non-conductive elongated body and at least one conductive wing extending laterally therefrom.

In one embodiment, the distal tip may be tapered so that the first electrode extends to a sharp tip thereof to concentrate a current density thereto.

In one embodiment, the first electrode may extend about the distal opening of the lumen.

In one embodiment, the first electrode may extend proximally into the lumen from the distal opening.

In one embodiment, the first and second electrode may extend helically about the distal tip and may be separated from one another by an insulated portion.

In one embodiment, the device may further comprise a second needle slidably received within a channel of the first needle, a distal end of the second needle configured to cauterize tissue.

In one embodiment, the distal end of the second needle may be one of hook-shaped, cross-shaped and circular.

The present disclosure is also directed to a system for treating target tissue, comprising a catheter including an elongated body and a distal tip, the elongated body extending from a proximal end to a distal end and including a lumen extending therethrough, the distal tip connected to the distal end of the elongated body and including a first electrode and a second electrode extending thereabout, the first electrode extending to a distal opening of the lumen and a power source supplying a current to the first electrode. The system also comprises a needle extending longitudinally from a proximal end to a distal end, the needle slidably received within the lumen of the catheter to be moved between a retracted bipolar configuration, in which the distal end of the needle is proximal the distal opening of the catheter so that when the distal tip is pressed against the target tissue the current is passed from the first to second electrode to coagulate the target tissue, and an extended monopolar configuration, in which the distal end of the needle extends distally past the distal opening of the catheter so that the needle contacts the first electrode and inactivates the second electrode to cut the target tissue, and a handle assembly connected to the proximal end of the catheter and including an actuator for moving the needle between the retracted bipolar configuration and the extended monopolar configuration.

The present disclosure is also directed to a method for treating tissue, comprising inserting a catheter of a device into a living body until a distal tip thereof is proximate a target site, the distal tip including a first electrode and a second electrode extending thereabout, providing current to the first electrode and pressing the distal tip against a first tissue at the target site, moving a needle housed within the catheter from a retracted bipolar configuration, in which a distal end of the needle is proximal a distal opening of a lumen of the catheter, to an extended monopolar configuration, in which the distal end of the needle extends distally past the distal opening of the lumen to contact the first electrode which extends to the distal opening, and pressing the distal end of the needle against a second target tissue at the target site to cut the second target tissue.

In one embodiment, the method may further comprise injecting one of a fluid and a drug through a channel of the needle to the target site.

In one embodiment, the method may further comprise providing a suctioning force through a channel of the needle.

In one embodiment, pressing the distal tip against the first tissue may coagulate the first tissue.

In one embodiment, a distal end of the distal tip is tapered so that pressing the distal tip against the first tissue cuts the first tissue.

BRIEF DESCRIPTION

FIG. 9D shows a longitudinal side view the device of FIG. 9A according to yet another alternate embodiment of the present disclosure;

FIG. 9E shows a longitudinal side view the device of FIG. 9A according to another alternate embodiment of the present disclosure;

DETAILED DESCRIPTION

Figure 1A:
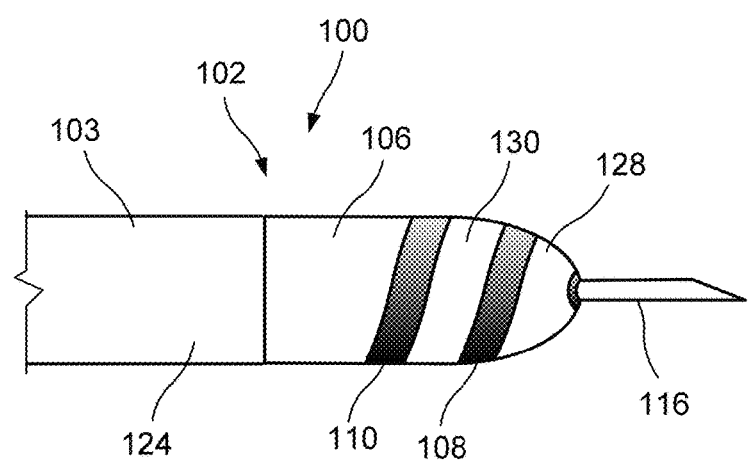
FIG. 1A shows a longitudinal side view of a device according to an exemplary embodiment of the present disclosure.

The present disclosure may be further understood with reference to the following description and the appended drawings, wherein like elements are referred to with the same reference numerals. The present disclosure relates to endoscopic devices and, in particular, endoscopic devices capable of injecting, cutting and coagulation. Exemplary embodiments of the present disclosure describe a device movable between a monopolar configuration and a bipolar configuration so that the device is capable of use for both cutting and coagulation of tissue. In particular, exemplary embodiments describe a catheter including a distal tip with a pair of electrodes for bipolar electrical activation to coagulate tissue. A needle is slidable through the catheter so that, when the needle is extended distally out of the catheter, a return path of the bipolar configuration is blocked, and the needle has a monopolar electrical activation to cut tissue. Thus, a single device is capable of achieving multiple tissue treatments. It should be noted that the terms "proximal" and "distal", as used herein, are intended to refer to a direction toward (proximal) and away from (distal) a user of the device.

As shown in FIGS. 1-6, a device 100 for treating a target tissue comprises a catheter 102 including a lumen 104 extending longitudinally therethrough and a distal tip 106. The distal tip 106 includes a first electrode 108 and a second electrode 110 wound thereabout (e.g., circumferentially around the distal tip) and separated from one another by an electrically insulative material to form a bipolar arrangement. Thus, when the distal tip 106 is pressed against target tissue, energy may be provided to the distal tip 106 to heat and coagulate the target tissue. The device 100 further comprises a needle 116 slidably received within the lumen 104 of the catheter 102 and movable between an extended monopolar configuration in which a distal end 118 of the needle 116 extends distally from the lumen 104 and a retracted bipolar configuration in which the distal end 118 is withdrawn proximal into the lumen 104 via a distal opening 120. In the monopolar configuration, the needle 116 acts alone as a monopolar electrode while, in the bipolar configuration, the first and second electrodes 108, 110, respectively, operate together to apply bipolar energy to target tissue. As will be described in further detail below, the first (e.g., positive) electrode 108 is structured so that it extends to the distal opening 120 of the lumen 104 and, when the needle 116 is in the extended configuration, the needle 116 contacts the first electrode 108. Extension of the needle 116 to the extended configuration may also break a return path of the second electrode 110 so that the first electrode 108 provides monopolar activation of the needle 116. Thus, the needle 116, in the extended monopolar configuration, may be energized to cut target tissue when pressed thereagainst. When the needle 116 is in the retracted configuration, however, the first and second electrodes 108, 110 may be energized to provide bipolar activation of the distal tip 106 to coagulate tissue. In one embodiment, the needle 116 may be hollow, including a channel 122 extending therethrough so that the channel 122 may be used to pass fluid therethrough. Thus, the device 100, in various configurations, may be capable of injecting, cutting and/or coagulation. The device 100 enables a user (e.g., physician) to utilize multiple treatment options without having to remove, replace or insert additional devices.

The catheter 102 includes an elongated body 103 extending longitudinally from a proximal end 112 to a distal end 124 and a distal tip 106 at the distal end 124 of the elongated body 103. The lumen 104 extends longitudinally through the catheter 102, through both the elongated body 103 and the distal tip 106 to the distal opening 120 and is sized and shaped to slidably receive the needle 116 therein. The elongated body 103 may be sufficiently flexible so that the catheter 102 may be inserted through even tortuous paths of a living body via, for example, a working channel of an endoscope. The proximal end of the catheter 102 may be attached to a handle assembly 132 which includes an actuator (not shown) for moving the needle 116 between the extended monopolar configuration and the retracted bipolar configuration.

Figure 2:
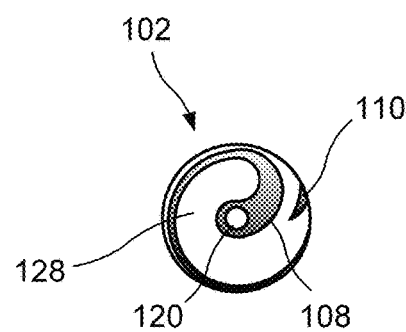
FIG. 2 shows a front view of the device of FIG. 1A, from a distal end of the device along a longitudinal axis of the device.
Figure 3:
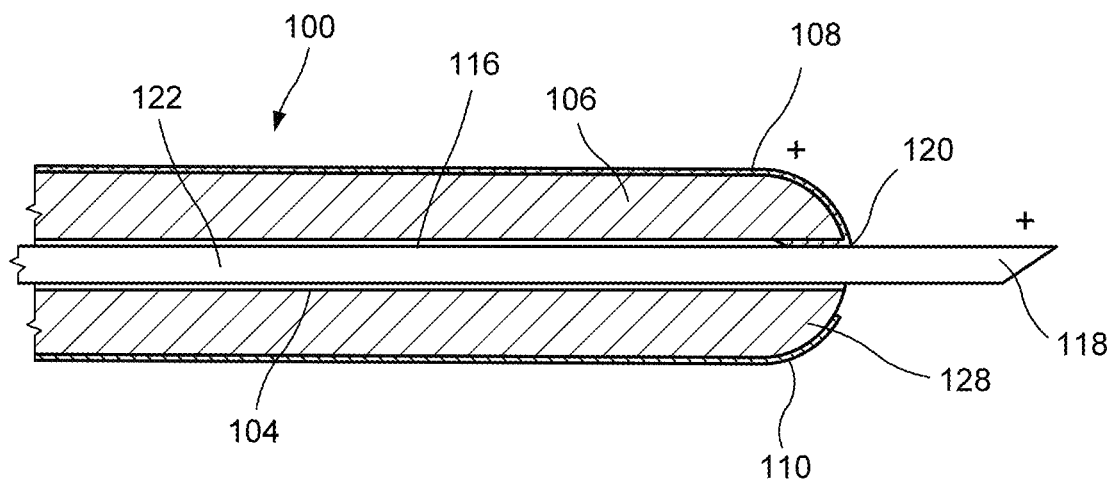
FIG. 3 shows an enlarged longitudinal cross-sectional view of a distal portion of the device of FIG. 1A, in an extended monopolar configuration.
Figure 4:
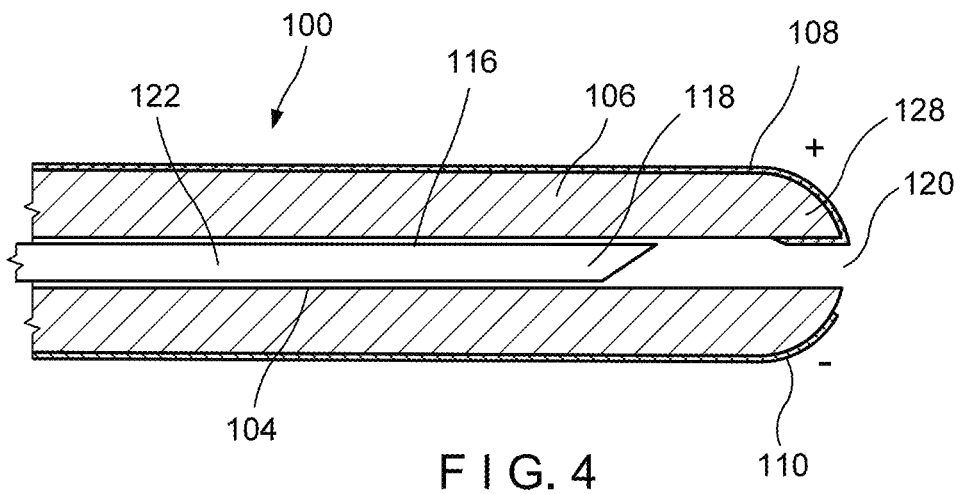
FIG. 4 shows an enlarged longitudinal cross-sectional view of the distal portion of the device of FIG. 1A, in a retracted bipolar configuration.

As would be understood by those skilled in the art, the distal tip 106 may be formed of any suitable biocompatible, electrically insulative material such as a ceramic with the first and second electrodes 108, 110 extending helically or spirally thereabout in the distal tip 106. The first and second electrodes 108, 110 may be formed of any suitable electrically conductive, biocompatible material such as, for example, gold. The first and second electrodes 108, 110 may be separated from one another via one or more electrically insulative areas 130. The bipolar electrode structure of the catheter 102 may be substantially similar to the electrode structure of the GOLD PROBE™ electrohemostasis catheter and of U.S. Pat. No. 5,403,311, the entire disclosure of which is incorporated herein by reference. As shown in FIGS. 2-4, the first electrode 108, however, may extend to the distal end of the distal tip 106 to at least partially surround the distal opening 120 of the catheter 102 so that the first electrode 108 contacts the needle 116, when the needle 116 is in the extended configuration. In a further embodiment, the first electrode 108 may also extend proximally into the lumen 104 from the distal opening 120. The first and second electrodes 108, 110 may extend about and/or along the distal tip 106 in any of a variety of other configurations (e.g., longitudinal strips, circumferential bands, helical windings, etc.) so long as the first electrode 108 extends to the distal opening 120 of the catheter 102 to contact the needle 116, when the needle 116 is in the extended configuration.

A distal end 128 of the distal tip 106 may have any of a variety of configurations. In one exemplary embodiment, the distal face 128 may be rounded (e.g., hemispherical). In another embodiment, the distal face 128 may be substantially planar. The distal face 128 may have any of a variety of shapes so long as the distal tip 106 is configured to coagulate tissue with which it is in contact when energized.

Figure 5:
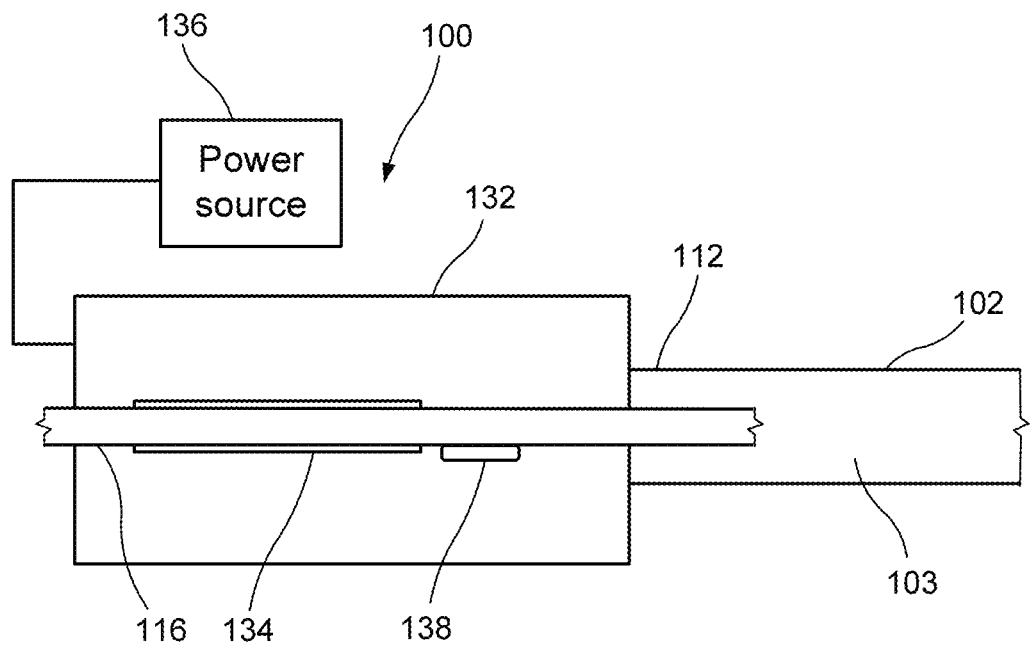
FIG. 5 shows a partial longitudinal cross-sectional view of a proximal portion of the device of FIG. 1A, in the bipolar configuration.
Figure 6:
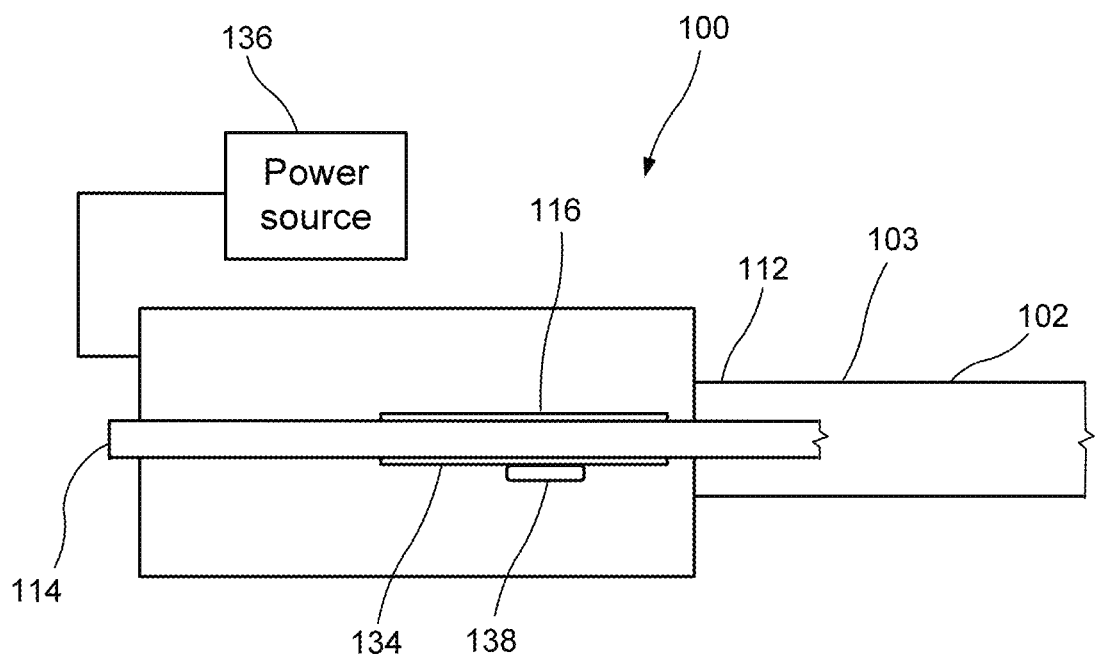
FIG. 6 shows a partial longitudinal cross-sectional view of the proximal portion of the device of FIG. 1A, in the monopolar configuration.

As shown in FIGS. 5 and 6, the first electrode 108 may be powered via a power source 136 connected to a proximal end of the device 100. The second electrode 110 may be electrically connected to a conductive pad 138 pressed into contact with a proximal portion of the needle 116, which is housed within the handle assembly 132, to provide a return path for the current. In one exemplary embodiment, the pad 138 may be biased toward the needle 116 via, for example, a spring or other biasing element. In other embodiments, however, the return may be connected to the needle 116 in any of a number of different ways. For example, the return may be connected to the needle 116 via a ring, a support built into the handle assembly 132, a clip, etc.

Figure 1B:
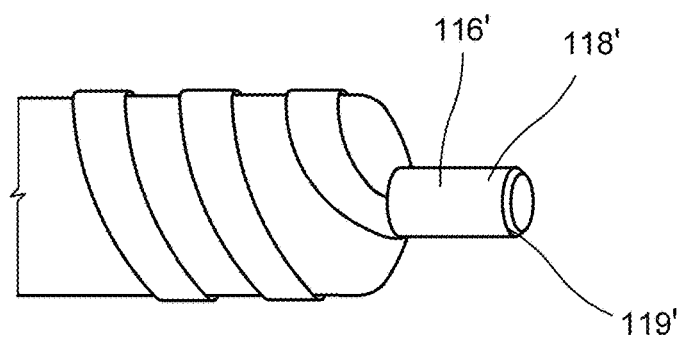
FIG. 1B shows a longitudinal side view of a device according to another exemplary embodiment of the present intention.

The needle 116 extends longitudinally from a proximal end 114 to the distal end 118 and includes the channel 122 extending longitudinally therethrough. The needle 116 is slidably received within the lumen 104 so that the needle 116 is movable relative thereto between the extended monopolar configuration and the retracted bipolar configuration. The proximal end 114 may extend proximally from the proximal end 112 of the catheter 102 so that the proximal end 114 extends through the handle assembly 132. The proximal end 114 may extend proximally from the handle assembly 132 and may be configured to be connected to a fluid source for the injection of fluids and/or drugs. In another embodiment, the proximal end 114 may be connected to a vacuum source which may apply a suction force therethrough. A proximal portion of the needle 116 is connected to an actuator of the handle assembly 132 so that the needle 116 may be moved between the monopolar and bipolar configurations via the actuator. The distal end 118 of the needle 116, as shown in FIG. 1A, may include a tapered tip for facilitating cutting of tissue when the distal end 118 of the needle 116 is pressed against tissue. Alternatively, as shown in FIG. 1B, a distal end 118' needle 116' may be non-tapered so that a distal face 119' thereof is substantially perpendicular to a longitudinal axis of the needle 116'. In one embodiment, the distal face 119' may include a sharpened edge.

In one exemplary embodiment, the needle 116 is formed of an electrically conductive material so that, when the needle 116 contacts the first electrode 108, the needle 116 is electrically activated. Those skilled in the art will understand that the needle 116 may, alternatively, be permanently mechanically coupled to a source of electric power and energized and de-energized via a switch on a handle or any other actuator. The needle 116 may include an insulated portion 134 along a portion of the needle 116 received within the handle assembly 132. The insulated portion 134 may be insulated via, for example, an insulating sheath, or may be formed of a non-conductive material. The insulated portion 134 is positioned along the needle 116 so that, when the needle 116 is in the retracted bipolar configuration, the insulated portion 134 is proximal of the pad 138 and is not in contact therewith. When the needle 116 is moved distally relative to the handle assembly 132, toward the extended monopolar configuration, however, the insulated portion 134 extends over the pad 138 to break the return path of the current, inactivating the second electrode 110. Thus, moving the needle 116 to the extended configuration may automatically inactivate the return, causing the device 100 to be moved from the bipolar configuration to the monopolar configuration.

Although the return path is described as being broken by the movement of the needle 116 from the retracted configuration to the extended configuration, the return path may inactivated in any of a number of ways. For example, the return path may be disconnected by a pushbutton, toggle switch, or any other switching mechanism. It is not required that the longitudinal movement of the needle 116 relative to the catheter 102 facilitates the making/breaking of the return path.

According to an exemplary method using the device 100, the catheter 102 is inserted into a patient's body along a tortuous path through, for example, a working channel of a flexible endoscope, until the distal tip 106 is proximate a target site. The catheter 102 is generally inserted to the target site with the needle 116 in the retracted configuration to avoid injury and/or damage to the working channel of the endoscope. Once the catheter 102 has reached the target site, the power source 136 may be powered on to supply energy to the first electrode 108. Thus, when the distal tip 106 is pressed into contact with tissue at the target site, current is passed from the first electrode 108 to the second electrode 110 to heat and coagulate target tissue via a bipolar activation. Where it is desired to cut tissue at the target site, the needle 116 may be moved distally relative to the catheter 102 toward the extended configuration. As described above, extending the needle 116 inactivates the second electrode 110 to switch the device from the bipolar configuration to the monopolar configuration. In particular, when the needle 116 is extended distally past the distal opening 120 of the lumen 104 of the catheter 102, the needle 116 contacts the first electrode 108 so that current passes to the needle 116 to provide a monopolar activation thereof. Thus, the needle 116 may be used to cut tissue at the target site.

In some embodiments, as would be understood by those skilled in the art, a stylet (not shown) may be received within the channel 122 of the needle 116 to prevent the collection of charred tissue therein during the cutting process. In other embodiments, as described above, fluid and/or drugs may be injected to the target site through the channel 122 of the needle 116. Alternatively, vacuum pressure may be applied through the channel 122 to provide suctioning to the target site to draw tissue against the distal tip 106. The device 100 may be moved between the retracted bipolar configuration and the extended monopolar configuration to coagulate and cut tissue, respectively, as desired. Once the target site has been treated, as desired, the power source 136 may be powered off and the needle 116 may be withdrawn proximally into the catheter 102 so that the device 100 may be removed from the body.

Figure 7:
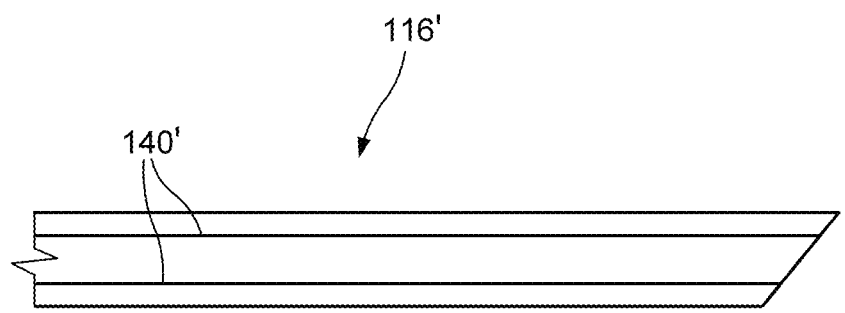
FIG. 7 shows a longitudinal side view of a needle according to an alternate embodiment of the present disclosure.
Figure 8:
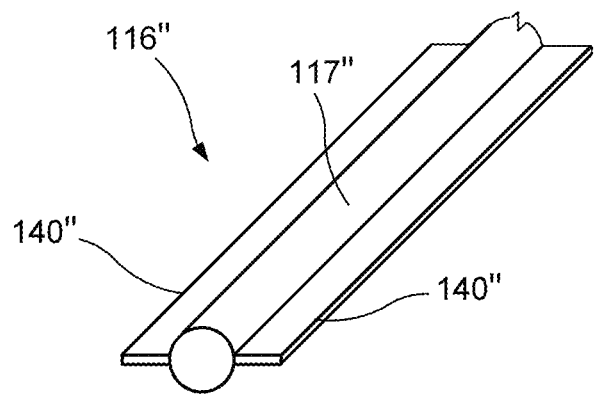
FIG. 8 shows a perspective view of a needle according to another alternate embodiment of the present disclosure.

Although the needle 116 is described as formed of an electrically conductive material, in alternate embodiments, a needle of the device 100 may be formed of material that is not electrically conductive except that it will include small conductive portions in desired locations to facilitate cutting by increasing current density at these locations. For example, as shown in FIG. 7, a needle 116' may include metal strips 140' extending along a length thereof so that, when the needle 116' is extended distally past the distal opening 120 of the catheter 102, the metal strips 140' are activated via the first electrode 108. In another embodiment, as shown in FIG. 8, a needle 116" may include one or more conductive wings 140" extending from a non-conductive needle body 117". The needles 116' and 116" are exemplary only. Needles of the device 100 may have a variety of configurations for facilitating cutting via increasing a current density therealong.

Figure 9A:
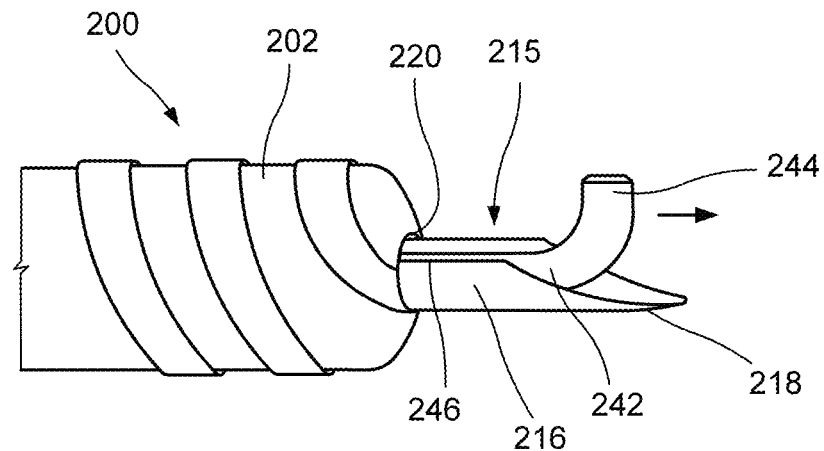
FIG. 9A shows a longitudinal side view of a device according to another exemplary embodiment of the present disclosure.
Figure 9B:
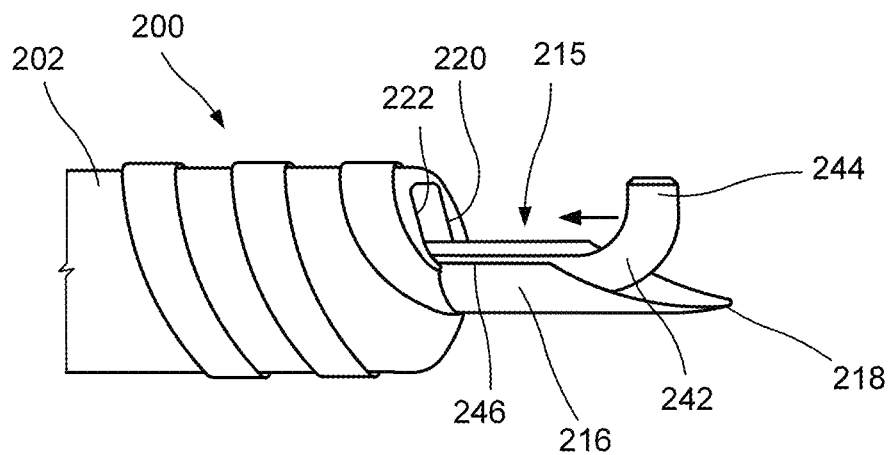
FIG. 9B shows a longitudinal side view the device of FIG. 9A according to an alternate embodiment of the present disclosure.
Figure 9C:
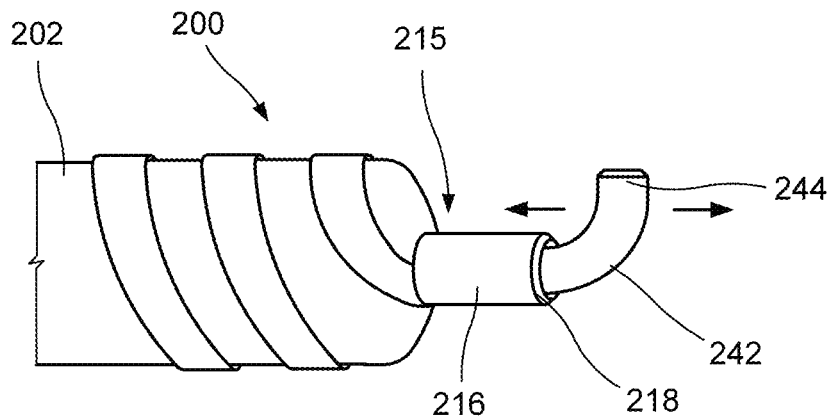
FIG. 9C shows a longitudinal side view the device of FIG. 9A according to another alternate embodiment of the present disclosure.

In another embodiment, as shown in FIGS. 9A-9E, a device 200 may be substantially similar to the device 100 comprising a catheter 202 including a lumen through which a needle assembly 215 is slidably received so that the needle assembly 215 is movable relative thereto between a retracted bipolar configuration and an extended monopolar configuration. The needle assembly 215 includes a first needle 216 and a second needle 242 slidably received within a channel 222 of the first needle 216. The first needle 216 is substantially similar to the first needle 116 of the device 100, as described above and, in this embodiment, includes either a tapered distal tip 218 (as shown in FIGS. 9A and 9B) or a non-tapered distal tip (as shown in FIGS. 9C-9E). The second needle 242 may have a shape optimized for cutting efficiency and may be longitudinally movable relative to the first needle 216.

In one exemplary embodiment, as shown in FIGS. 9A-9C, the second needle 242 is configured as a cauterizing hook. In particular, a distal end 244 of the second needle 242 is bent relative to a remaining portion of a length thereof so that the second needle 242 is substantially hook-shaped. The first needle 216, as shown in FIGS. 9A-9B, includes a longitudinal slot 246 extending along a length thereof to accommodate the bent distal end 244 of the second needle 242 when the second needle 242 is moved relative to the first needle 216. According to one example, as shown in FIG. 9A, proximal movement of the second needle 242 relative to the catheter 202 and/or the first needle 216 may be restricted via a size and shape of an opening 220 of the lumen 204 at a distal end 228 of the catheter 202 so that the second needle 242 cannot be drawn into the lumen of the catheter 202. According to another example, as shown in FIG. 9B, the opening 220 at the distal end 228 of the lumen is sized and shaped to permit the bent distal end 244 of the second needle 242 to be drawn proximally into and out of the lumen 204. According to yet another example, as shown in FIG. 9C, in which the first needle 216 does not include a longitudinal slot, the second needle 242 may not be drawn entirely into the channel 220 of the first needle 216.

Although FIGS. 9A and 9B show a hook-shaped distal end 244 of the second needle 242, the distal end 244 of the second needle 242 may have any of a variety of configurations to optimize cutting efficiency. For example, the distal end 244 may have a cross-shape, as shown in FIG. 9D, or a planar circular shape, as shown in FIG. 9E. The described features for each of the catheter 202, the first needle 216 and the second needle 242 should not be limited to the embodiments shown in the FIGS. 9A-9E. Rather, the various features of the catheter 202, the first needle 216 and the second needle 218 may be combined in any of a variety of different configurations, as desired.

Figure 10:
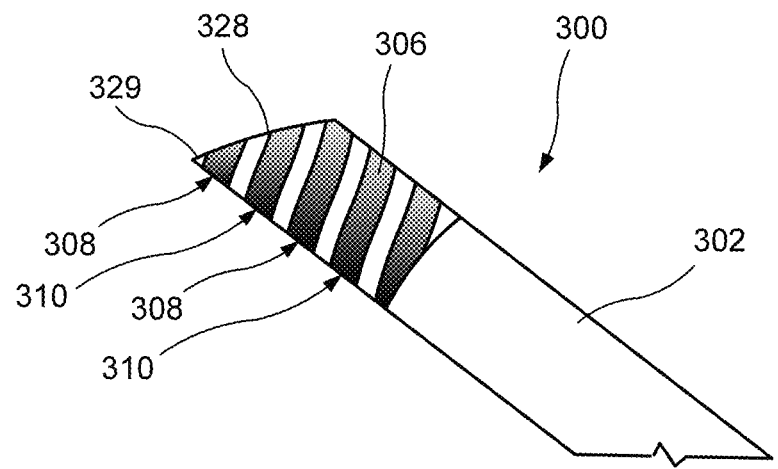
FIG. 10 shows a longitudinal side view of a device according to yet another exemplary embodiment of the present disclosure.

Although the above exemplary embodiments describe moving the device between a bipolar coagulating configuration and a monopolar cutting configuration, in another embodiment, a distal tip of a catheter may be optimized for cutting so that a device may be movable between two cutting configurations. For example, as shown in FIG. 10, a device 300 may be substantially similar to the device 100 described above, comprising a catheter 302 including a distal tip 306 having a first (e.g., positive) and second (e.g., negative) electrode 308, 310 extending thereabout. Although not shown, the device 300 may further comprise a needle received slidably therein so that the needle is movable between a retracted configuration, in which a distal end of the needle is proximal a distal end 328 of the distal tip 306, and an extended configuration, in which the distal end of the needle is distal of the distal end 328 of the distal tip 306. The catheter 302 is substantially similar to the catheter 102. The distal tip 306, however, is tapered via a single grind so that a distal end 328 tapers to a sharp tip 329. The first electrode 308 extends to the sharp tip 329 to concentrate a current density thereto to facilitate a cutting via the catheter 302. Thus, rather than achieving coagulation, as described above with respect to the device 100, the catheter 302 may be used to cut tissue via the sharp tip 329. The needle of the device 300 is therefore not required to cut tissue. In some embodiments, however, the needle may be moved between the retracted configuration, so that the catheter 302 may provide cutting, and the extended configuration, so that the needle provides cutting, to provide the device 300 with two cutting methods with two different cutting characteristics.

Figure 11:
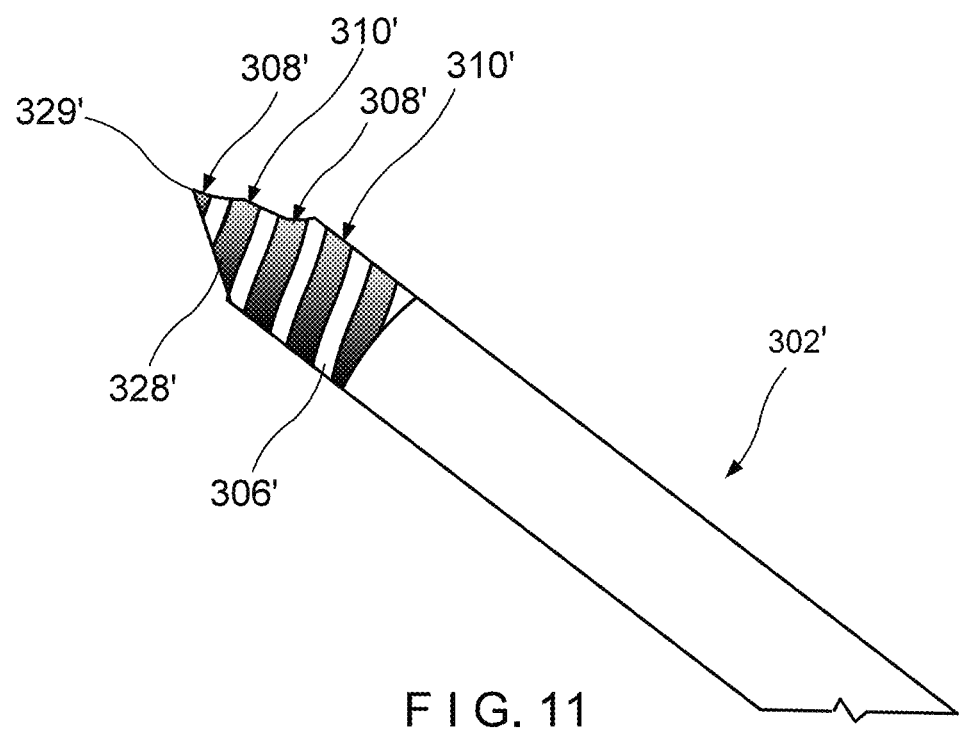
FIG. 11 shows a longitudinal side view of a catheter according to an alternate embodiment of the present disclosure.

In another example, as shown in FIG. 11, according to a device that is substantially similar to the device 300 described above, a catheter 302' may include a distal tip 306' including first and second electrodes 308', 310' extending thereabout in a bipolar configuration. Similarly to the distal end 328 of the distal tip 306 described above, the distal end 328' of the distal tip 306' has a tapered distal end 328'. The distal end 328', however, may be tapered to a sharp tip 329' via a double grind. Similarly to the distal tip 306, the first electrode 308' extends to the sharp tip 329' to facilitate cutting thereby by concentrating a current density thereto.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A device for treating tissue, comprising:
a catheter including an elongated body and a distal tip, the elongated body extending from a proximal end to a distal end and including a lumen extending therethrough, the distal tip connected to the distal end of the elongated body and including a first electrode and a second electrode extending thereabout, the first electrode extending to a distal opening of the lumen; and
a first needle extending longitudinally from a proximal end to a distal end, the first needle received within the lumen of the catheter for movement between a bipolar configuration, in which the distal end of the first needle is in a first position relative to the distal opening of the catheter, and an extended monopolar configuration, in which the distal end of the first needle is in a second position,
wherein, in the first position, the distal end of the first needle is proximal of a distal opening of the lumen of the distal tip of the catheter, and wherein, in the second position the first needle contacts the first electrode and is configured to cut the tissue,
wherein the first electrode is connectable to a power source for supplying a current thereto, and
wherein the second electrode is electrically connected to a proximal portion of the first needle to provide a return path for current.

2. The device of claim 1, wherein, when in the second position, the distal end of the first needle is distal of the distal end of the lumen of the catheter.

3. The device of claim 1, wherein the second electrode is connected to the proximal portion of the first needle via a conductive pad biased against the first needle.

4. The device of claim 3, wherein the first needle is formed of a conductive material and includes an insulated portion which, when the first needle is in the extended monopolar configuration extends over the conductive pad to break the return path and inactivate the second electrode.

5. The device of claim 1, wherein the first needle includes a channel extending longitudinally therethrough and the proximal end of the first needle is configured to be coupled to one of a fluid source and a vacuum source.

6. The device of claim 5, wherein the channel of the first needle extends to distal end of the first needle.

7. The device of claim 5, wherein an opening between the channel and an exterior of the first needle has a proximal end separated from the distal end of the first needle.

8. The device of claim 7, wherein the opening between the channel and the exterior of the first needle extends from the proximal end of the opening to a distal end at the distal end of the first needle.

9. The device of claim 1, wherein the first needle is formed of a non-conductive material and includes a metal strip extending along a length thereof.

10. The device of claim 1, wherein the first needle is permanently connected to a source of electrical energy, the device further including a first switch operable by a user to selectively energize and de-energize the first needle.

11. The device of claim 1, the device further including a second switch operable by a user to selectively complete and sever a return path of current to the first needle to switch the first needle from a bi-polar mode of operation to a monopolar mode of operation.

12. The device of claim 1, wherein the first needle includes a non-conductive elongated body and at least one conductive wing extending laterally therefrom.

13. The device of claim 1, wherein the distal tip is tapered so that the first electrode extends to a sharp tip thereof.

14. The device of claim 1, wherein the first electrode extends about the distal opening of the lumen.

15. The device of claim 1, wherein the first electrode extends proximally into the lumen from the distal opening.

16. The device of claim 1, wherein the first and second electrode extend helically about the distal tip and are separated from one another by an insulated portion.

17. The device of claim 1, further comprising a second needle slidably received within a channel of the first needle, a distal end of the second needle configured to cauterize the tissue.

* * * * *